(12) United States Patent
Drake et al.

(10) Patent No.: US 12,194,257 B2
(45) Date of Patent: Jan. 14, 2025

(54) SHUTTLE APPARATUS AND ASSOCIATED SYSTEMS AND METHODS

(71) Applicant: Medtronic, Inc., Minneapolis, MN (US)

(72) Inventors: Ronald A. Drake, St. Louis Park, MN (US); Matthew D. Bonner, Plymouth, MN (US); Trent M. Fischer, St. Paul, MN (US); Carla C. Pfeiffer, Anoka, MN (US); Brian P. Colin, Anoka, MN (US); Lester O. Stener, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 610 days.

(21) Appl. No.: 17/645,237

(22) Filed: Dec. 20, 2021

(65) Prior Publication Data

US 2022/0184350 A1 Jun. 16, 2022

Related U.S. Application Data

(62) Division of application No. 15/873,153, filed on Jan. 17, 2018, now Pat. No. 11,207,504.

(Continued)

(51) Int. Cl.
*A61M 25/09* (2006.01)
*A61M 25/01* (2006.01)
(Continued)

(52) U.S. Cl.
CPC ...... *A61M 25/09041* (2013.01); *A61M 25/01* (2013.01); *A61M 25/0105* (2013.01);
(Continued)

(58) Field of Classification Search
CPC ............. A61M 25/01; A61M 25/0105; A61M 25/09041; A61M 2025/0177;
(Continued)

(56) References Cited

U.S. PATENT DOCUMENTS 5,046,497 A 9/1991 Millar
11,207,504 B2 12/2021 Drake et al.
(Continued)

FOREIGN PATENT DOCUMENTS

CN 102238977 A 11/2011
CN 102802492 A 11/2012
(Continued)

OTHER PUBLICATIONS (PCT/US2018/014035) PCT International Preliminary Report on Patentability and Written Opinion of the International Searching Authority, dated Jul. 23, 2019, 8 pages.

(Continued)

*Primary Examiner* — Tiffany Legette

(74) *Attorney, Agent, or Firm* — Shumaker & Sieffert, P.A.

(57) ABSTRACT

The present disclosure is directed to a shuttle apparatus for detachably joining a catheter to a guidewire so that the joined catheter, extending alongside the guidewire, is in sliding engagement with the guidewire without extending around the guidewire. The apparatus comprises a collar member sized for mounting in sliding engagement around a length of the guidewire, the collar member having a longitudinal axis that approximately aligns along the length, (Continued)

when mounted thereabout, the length being defined between a proximal-most point of the guidewire and a distal point of the guidewire, the distal point being offset proximally from a distal-most point of the guidewire. The apparatus further comprises a plug member coupled to the collar member, the plug member having a longitudinal axis, and the plug member being sized to fit within an opening of the catheter for detachable engagement therewith.

16 Claims, 14 Drawing Sheets

Related U.S. Application Data

(60) Provisional application No. 62/447,121, filed on Jan. 17, 2017.

(51) Int. Cl.
*A61B 17/00* (2006.01)
*A61B 17/22* (2006.01)

(52) U.S. Cl.
CPC .............. *A61B 17/00234* (2013.01); *A61B 2017/00247* (2013.01); *A61B 2017/00867* (2013.01); *A61B 2017/22044* (2013.01); *A61M 2025/0177* (2013.01); *A61M 2025/09125* (2013.01)

(58) Field of Classification Search
CPC ......... A61M 2025/09125; A61M 2025/09041; A61B 2017/22044; A61B 2017/00247
See application file for complete search history.

(56) References Cited

U.S. PATENT DOCUMENTS

| | | |
|---|---|---|
| 2002/0072732 A1 | 6/2002 | Jung et al. |
| 2002/0077583 A1 | 6/2002 | Clemens et al. |
| 2012/0172690 A1 | 7/2012 | Anderson et al. |
| 2014/0324026 A1 | 10/2014 | Chrisman |
| 2014/0378992 A1 | 12/2014 | Ollivier |
| 2015/0094668 A1 | 4/2015 | Wood et al. |
| 2018/0168687 A1 | 6/2018 | Drake et al. |

FOREIGN PATENT DOCUMENTS

| | | |
|---|---|---|
| CN | 105492063 A | 4/2016 |
| CN | 105592885 A | 5/2016 |
| CN | 106028993 A | 10/2016 |

OTHER PUBLICATIONS

Notice of First Chinese Office Action, Application No. 201880006364.7.

Prosecution History from U.S. Appl. No. 15/873,153, now issued U.S. Pat. No. 11,207,504, dated Jun. 12, 2020 through Sep. 20, 2021, 40 pp.

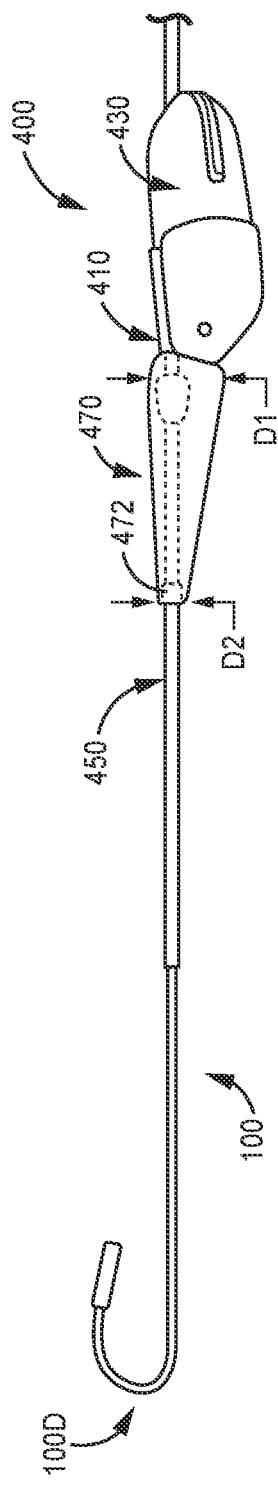
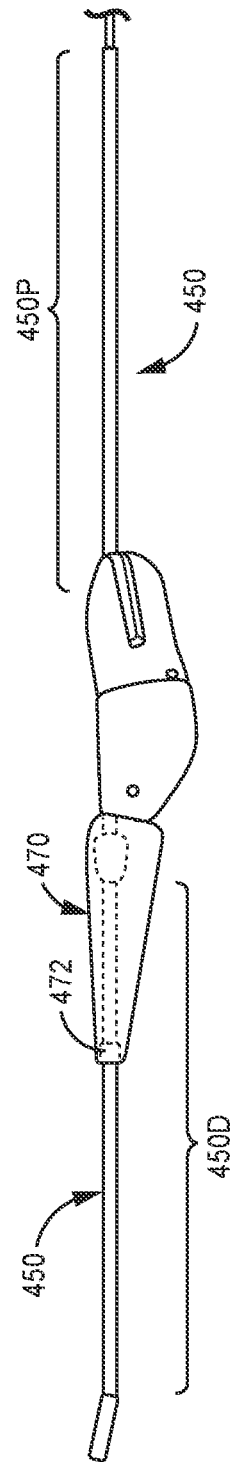
FIG. 1A
FIG. 1B

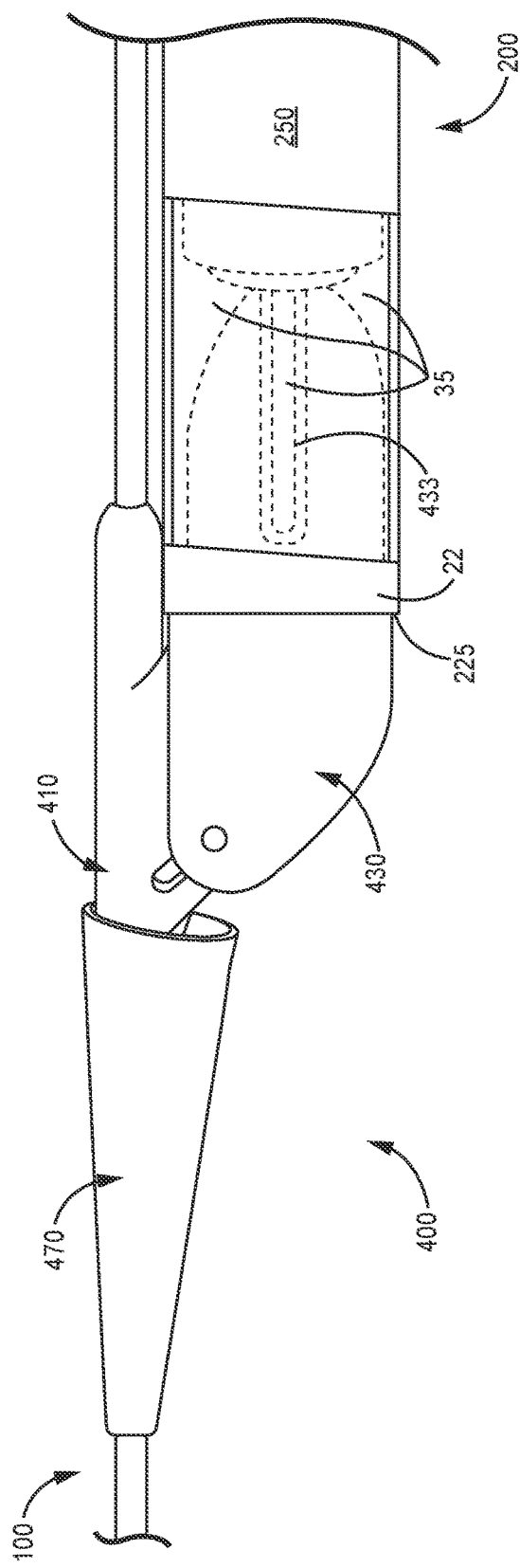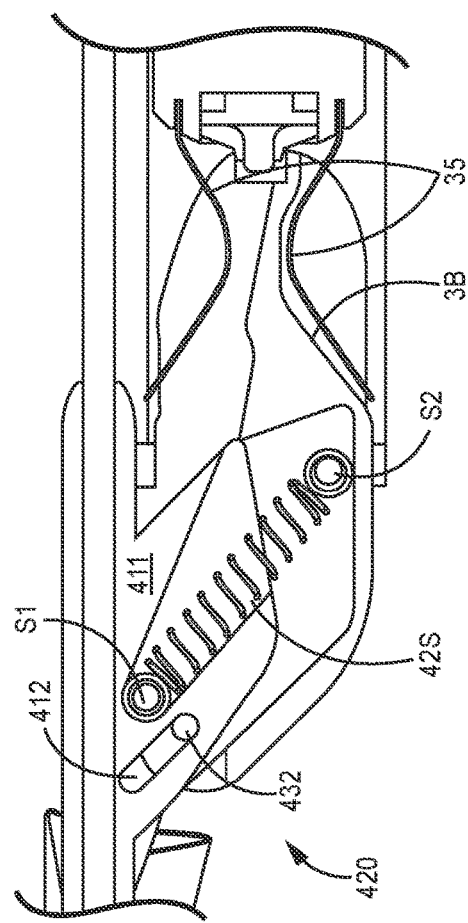
FIG. 5A
FIG. 5B

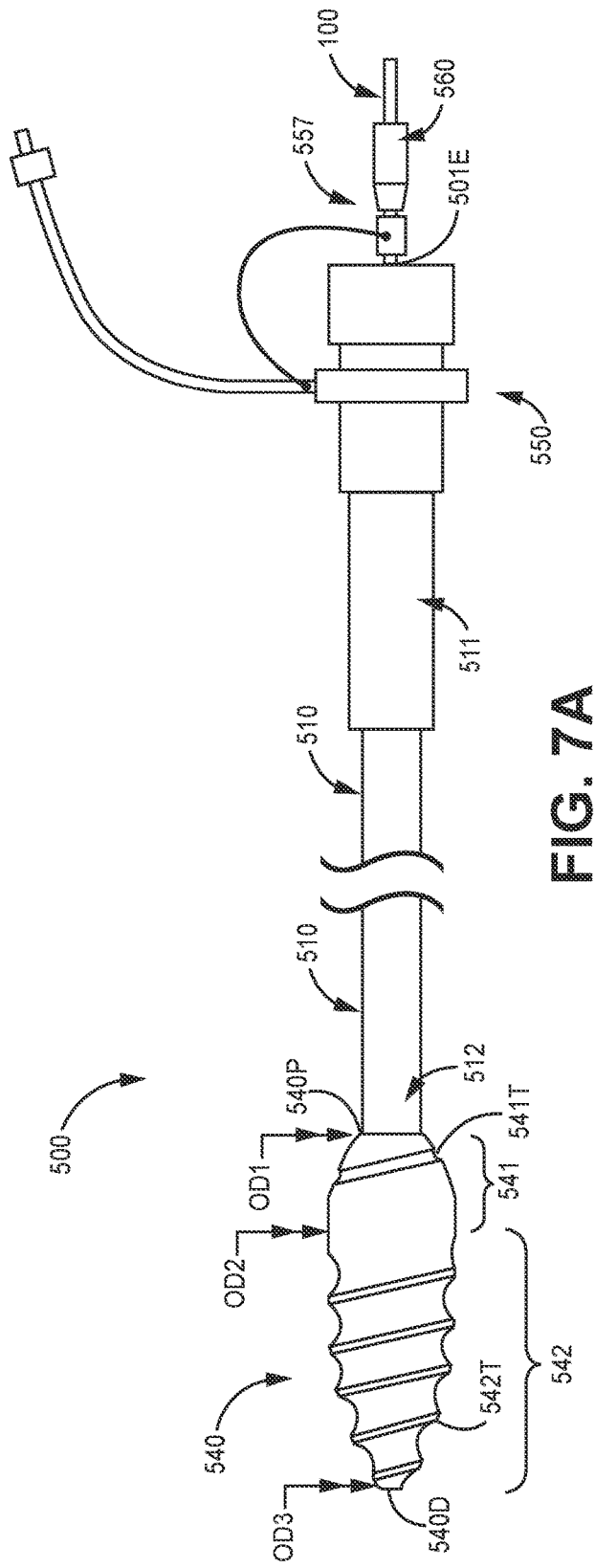
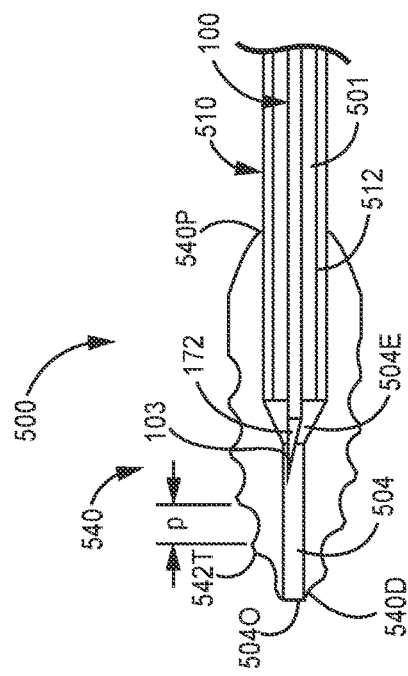
FIG. 7A
FIG. 7B

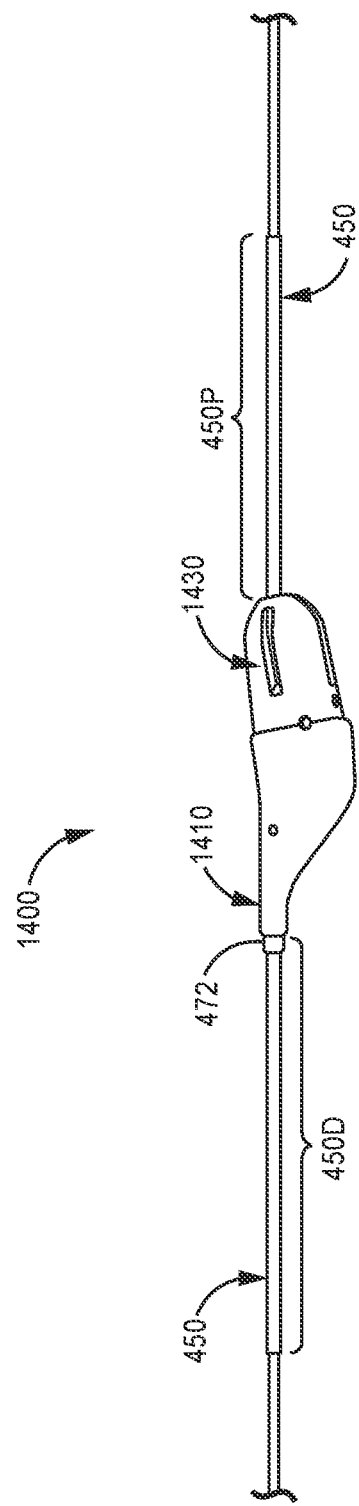

SHUTTLE APPARATUS AND ASSOCIATED SYSTEMS AND METHODS

This application is a divisional of U.S. patent application Ser. No. 15/873,153, filed Jan. 17, 2018, which claims the benefit of U.S. provisional patent application No. 62/447,121, filed Jan. 17, 2017, the entire contents of each of which are incorporated herein by reference.

FIELD OF THE DISCLOSURE

The present disclosure pertains to shuttle apparatus for detachably joining a catheter to a guide wire, and interventional medical systems methods that employ such an apparatus.

BACKGROUND

Interventional guidewires, known to those skilled in the art of minimally invasive medical procedures, are useful for providing access to remote sites within a patient's body, for example, to deliver diagnostic and/or therapy devices to the sites. In many instances, a guidewire is inserted into the body and steered into position at a target site so that a catheter can be guided to the site over the guidewire. The catheter, as part of an interventional medical system, may be configured to deliver a medical device to the site.

BRIEF DESCRIPTION OF THE FIGURES

FIGS. 1A and 1B are plan views further illustrating the shuttle apparatus of FIG. 1;

FIG. 5A is a plan view illustrating the shuttle apparatus of FIG. 1 in conjunction with a guidewire, and the catheter and implantable medical device of FIGS. 4A and 4B;

FIG. 5B is a longitudinal cross-section view showing a fitted plug member and received tines of the implantable medical device of FIGS. 4A and 4B;

FIG. 7A is a plan view of a dilator apparatus, according to some embodiments;

FIG. 7B is a longitudinal cross-section view through a portion of the dilator apparatus of FIG. 7A;

FIGS. 10A-10C illustrate a shuttle assembly that includes a collar member having an enhanced taper.

DETAILED DESCRIPTION

Figure 1:
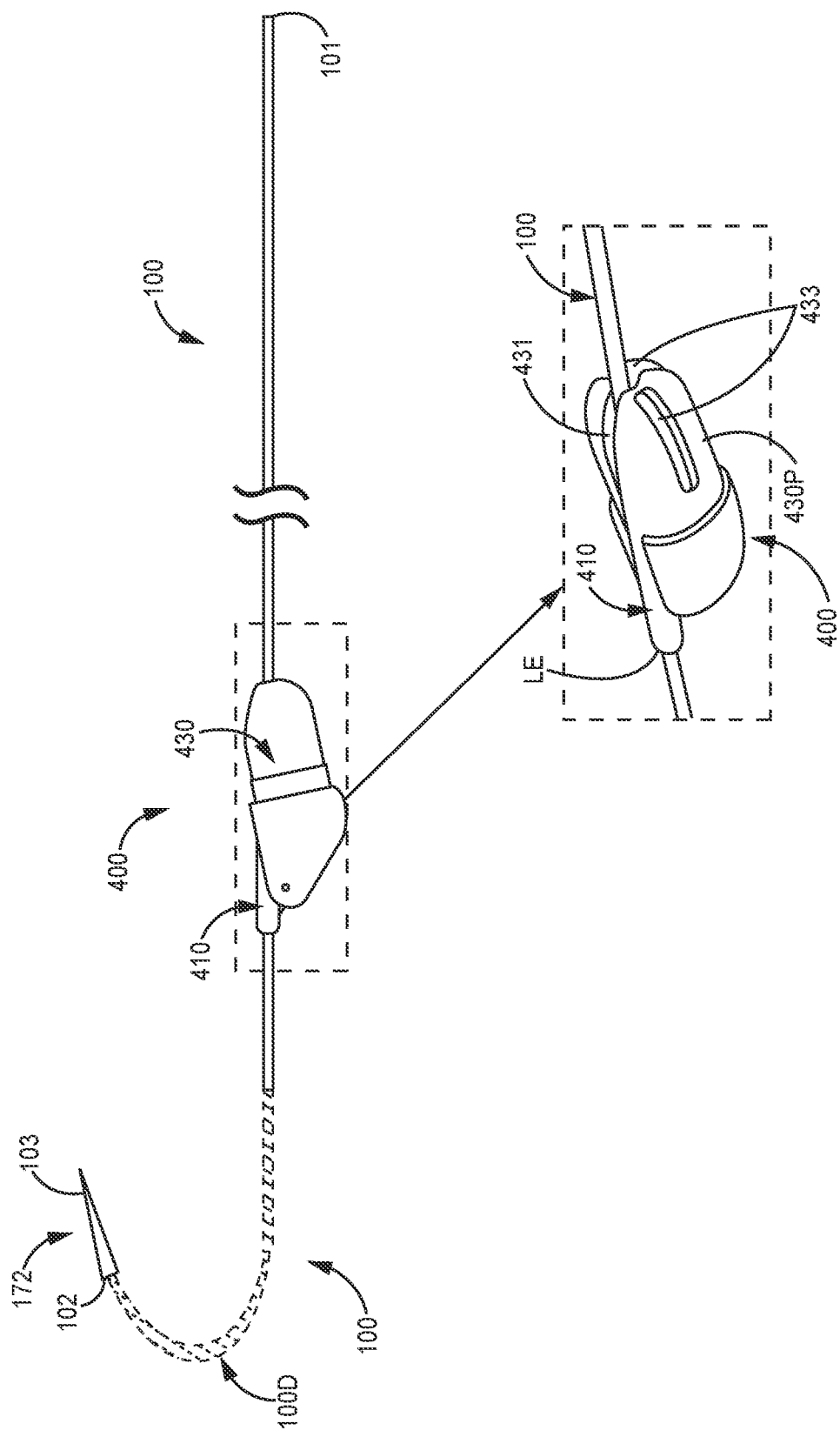
FIG. 1 is a plan view of a shuttle apparatus mounted around an exemplary guidewire.

The following detailed description is exemplary in nature and is not intended to limit the scope, applicability, or configuration of the invention in any way. Rather, the following description provides practical examples, and those skilled in the art will recognize that some of the examples may have suitable alternatives. Embodiments are described in conjunction with the appended drawings, illustrative thereof but not intended to limit the scope of the invention. In the drawings, like numerals denote like elements, and the drawings are not necessarily to scale.

FIG. 1 is a plan view of a shuttle apparatus 400 mounted around an exemplary guidewire 100, according to some embodiments, wherein apparatus 400 is configured to detachably join a catheter to guidewire 100, as will be described below, in conjunction with FIGS. 3, and 5A-B, so that the catheter can be shuttled along guidewire 100. FIG. 1 illustrates shuttle apparatus 400 including a collar member 410 and a plug member 430, which is rotatably coupled to collar member 410, for example, as described below in FIGS. 2, 2A-B. Collar member 410 and plug member 430 may each be formed from a relatively hard medical grade plastic, such as 72D PEBAX, Delrin or Nylon, for example, by injection molding. FIG. 1 further illustrates guidewire 100 extending over a length from a proximal-most point 101 thereof to a distal point 102 thereof, and including a distal tip 172 joined to the length at distal point 102, wherein distal tip 172 forms a piercing distal-most point 103 of guidewire 100. Collar member 410 of apparatus 400 is shown mounted around the length of guidewire 100, being in sliding engagement therewith. According to the illustrated embodiment, apparatus 400 is stopped from sliding over distal-most point 103 and off of guidewire 100 by an enlarged dimension of distal tip 172. According to some alternate embodiments, guidewire 100 includes an alternative type of distal tip, in lieu of tip 172, that forms a rounded or blunt distal-most point 103, but also has the enlarged dimension to prevent apparatus 400 from sliding over distal-most point 103 and off of guidewire 100. A significance of guidewire 100 with piercing distal-most point 103 formed by tip 172 is described below in conjunction with FIGS. 7B, 8A-B.

With further reference to FIG. 1, guidewire 100 may include a significantly flexible distal segment 100D that has a pre-formed J-shape and extends proximally from distal tip 172. The construction of such guidewires is known to those skilled in the art. In some embodiments, for example, as illustrated in FIGS. 1A-B, shuttle apparatus 400 further includes a collar extension 450, for example, to provide strain relief (e.g. a tapering stiffness) and to aid in tracking shuttle apparatus 400 along guidewire 100, which has a distal segment 450D extending distally from collar member 410, for example, over a length of about 2.5 cm-3 cm, and proximal segment 450P extending proximally from collar member 410, for example, over a length of about 2.5 cm-3 cm. According to some embodiments, extension 450 further extends within collar member 410, lining a lumen 401 thereof (FIG. 2B) and may be formed from stainless steel braid reinforced polyimide having a wall thickness of about 0.003 inch. As seen in FIG. 1B, when shuttle apparatus 400 is moved distally along wire 100, extension distal segment 450D straightens distal segment 100D from the aforementioned J-shape. According to some alternate embodiments, extension proximal segment 450P has a significantly longer length, for example, up to about 120 cm, so that an operator can maintain control over shuttle apparatus 400 outside a patient's body, for example, to pull apparatus 400 proximally along guidewire 100 and out from the patient's body; thus, the aforementioned enlarged dimension of distal tip 172 is not necessary in these embodiments. According to an exemplary embodiment, guidewire 100 may be a 0.035 inch J Tip Fixed core angiographic guide wire, such as is known to those skilled in the art, and distal tip 172 (e.g., formed from a medical grade stainless steel hypo-tube) is attached thereto for example, by crimping and/or welding methods known in the art.

FIGS. 1A-B further illustrate apparatus 400 including an optional nose cone 470 that tapers from a larger first diameter D1, at a proximal end thereof, to a smaller second diameter D2, at a distal end thereof. The proximal end of nose cone 470 is shown secured to a distal end of collar member 410, and the distal end of nose cone 470 may be secured to extension distal segment 450D. Nose cone 470 may be formed from a relatively soft medical grade polymer, such as, a thermoplastic elastomer (e.g., Chronoprene), a thermoplastic urethane (e.g., Tecoflex), or a thermoplastic vulcanizates (e.g., Santoprene). Nose cone 470 may include a radiopaque marker 472, for example, a 90/10 Pt/IR band, attached thereto in proximity to second diameter D2. In addition, collar member 410 and plug member 430 may be formed from a material that includes a radiopaque filler, for example, PEBAX with a tungsten additive. Nose cone 470, according to some embodiments, may provide additional strain relief and may be useful as described below, in conjunction with FIGS. 5A and 9A, but, according to some alternate embodiments, for example, as illustrated in FIGS. 10A-C, a leading edge LE of collar member 410 (FIG. 1) may be configured with an enhanced taper to eliminate the need for nose cone 470.

Figure 2:
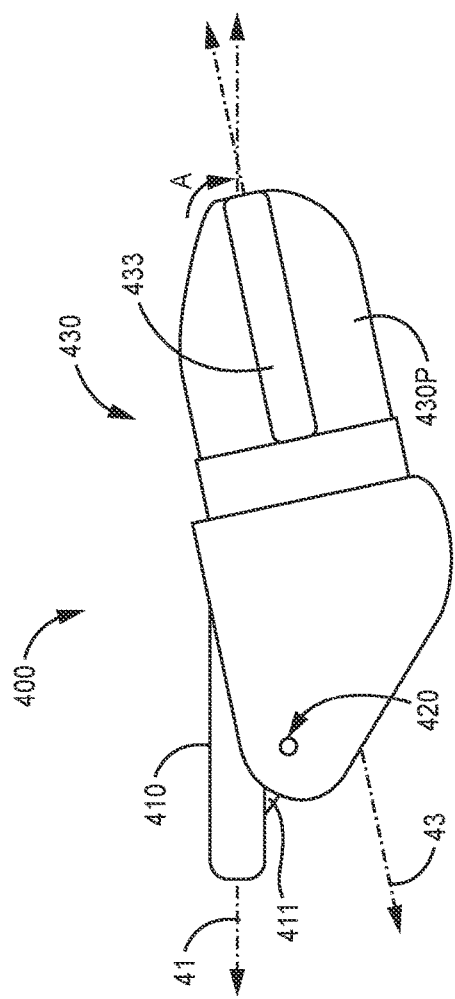
FIG. 2 is an enlarged plan view of the shuttle apparatus of FIG. 1.
Figure 2B:
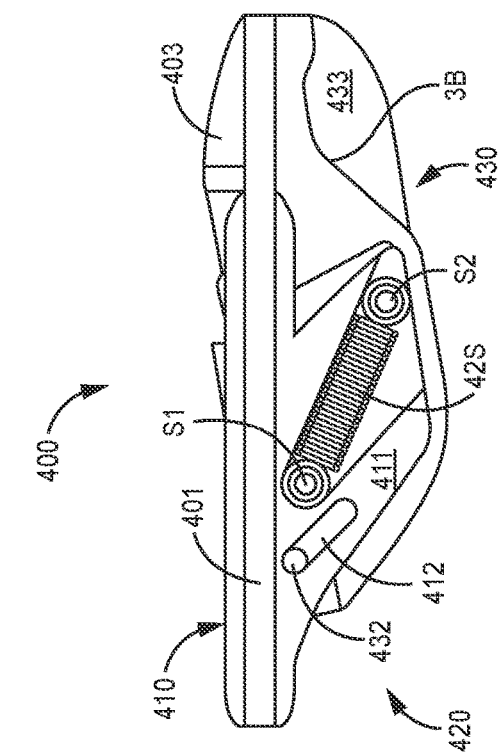
FIG. 2B is a cross-sectional view further illustrating the shuttle apparatus of FIG. 1.
Figure 2A:
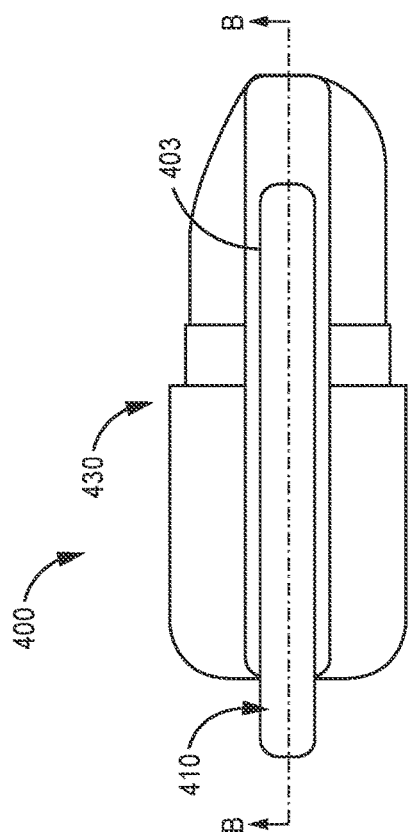
FIG. 2A is a plan view further illustrating the shuttle apparatus of FIG. 1.

FIG. 2 is an enlarged plan view of shuttle apparatus 400. FIG. 2 illustrates a pivot joint 420 of apparatus 400 rotatably coupling plug member 430 to collar member 410. According to the illustrated embodiment, pivot joint 420 allows plug member 430 to rotate per arrow A, relative to collar member 410, between an unengaging position, which is shown in FIG. 2, and an engaging position, which is shown in FIG. 3. With reference to FIG. 2, a longitudinal axis 43 of plug member 430 extends at an angle relative to a longitudinal axis 41 of collar member 410, when plug member 430 is in the unengaging position. The unengaging position of plug member 430 is also illustrated in FIGS. 1, 1A-B, where it can be seen that, when collar member 410 is mounted around the length of guidewire 100, longitudinal axis 41 of collar member 410 approximately aligns along the length, and plug member axis 43 crosses the length. With further reference to enlarged detail view of FIG. 1, and another plan view of shuttle apparatus 400 in FIG. 2A, plug member 430 preferably includes a longitudinally extending slot 403 that is sized to receive therein a portion of collar member 410 and the length of guidewire 100. With reference to FIG. 2A, collar member 410 in some embodiments extends along a longer length of plug member 430, although a shorter length of collar member 410 is shown in the cross-section view of FIG. 2B. In either case, the profile of shuttle apparatus 400 in the unengaging position is suitable for withdrawing shuttle apparatus from the patient's venous system, for example, as described below in conjunction with FIG. 9B.

Figure 3:
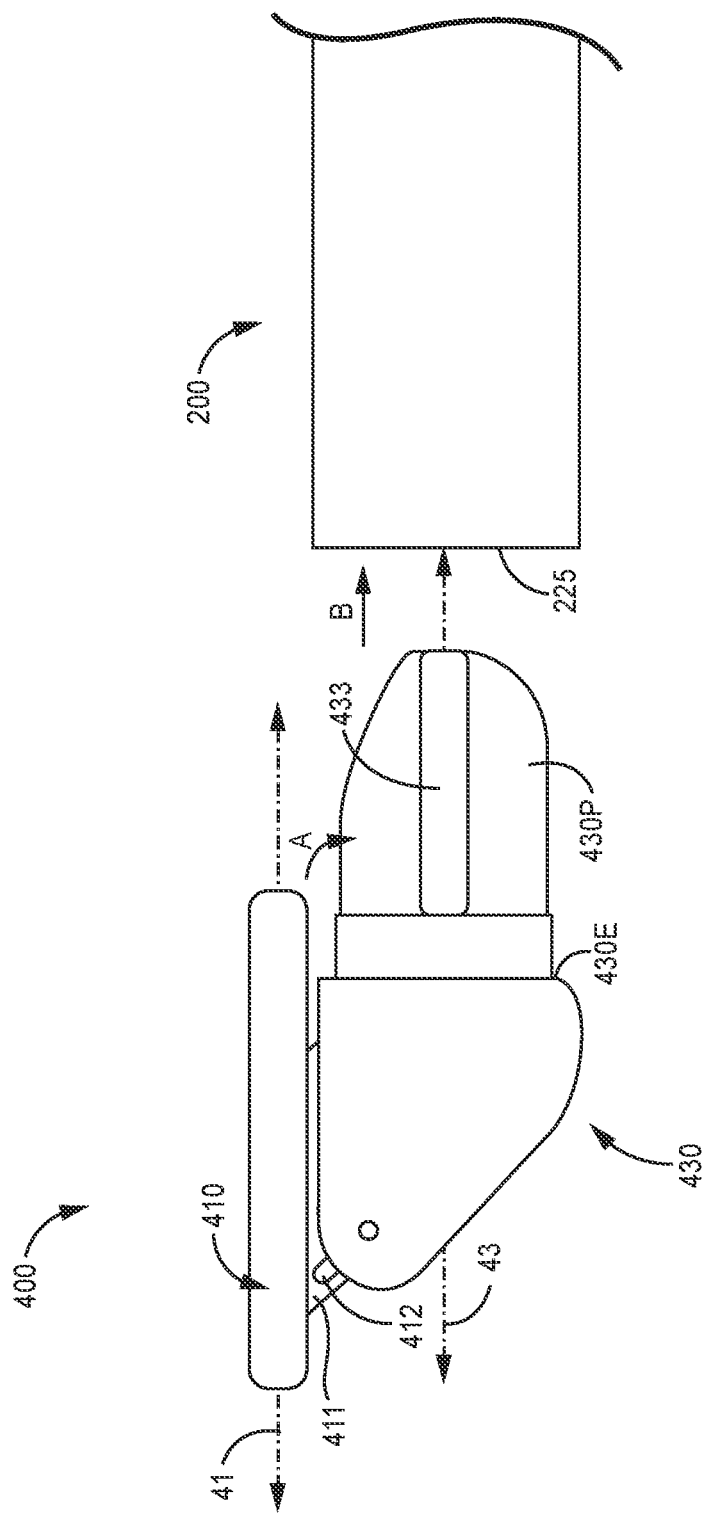
FIG. 3 is conceptual diagram illustrating a plug member of the shuttle apparatus of FIG. 1 rotated relative to a collar member of the shuttle apparatus of FIG. 1, and into the engaging position.

When plug member 430 is rotated relative to collar member 410, per arrow A, and into the engaging position shown in FIG. 3, longitudinal axis 43 of plug member 430 extends approximately parallel to longitudinal axis 41 of collar member 410, as shown in FIG. 3. Thus, plug member 430 may be inserted, per arrow B, into an opening 225 of a catheter 200 to detachably join shuttling apparatus 400 to catheter 200, for example, as illustrated in FIGS. 5A-B. The fit of plug member 430 within opening 225 is relatively 'snug', for example, being at least a line-to-line fit. FIG. 3 further illustrates a raised edge 430E of plug member 430, according to some embodiments, which limits a depth to which plug member 430 can extend past catheter opening 225 when fitted therein.

Figure 4A:
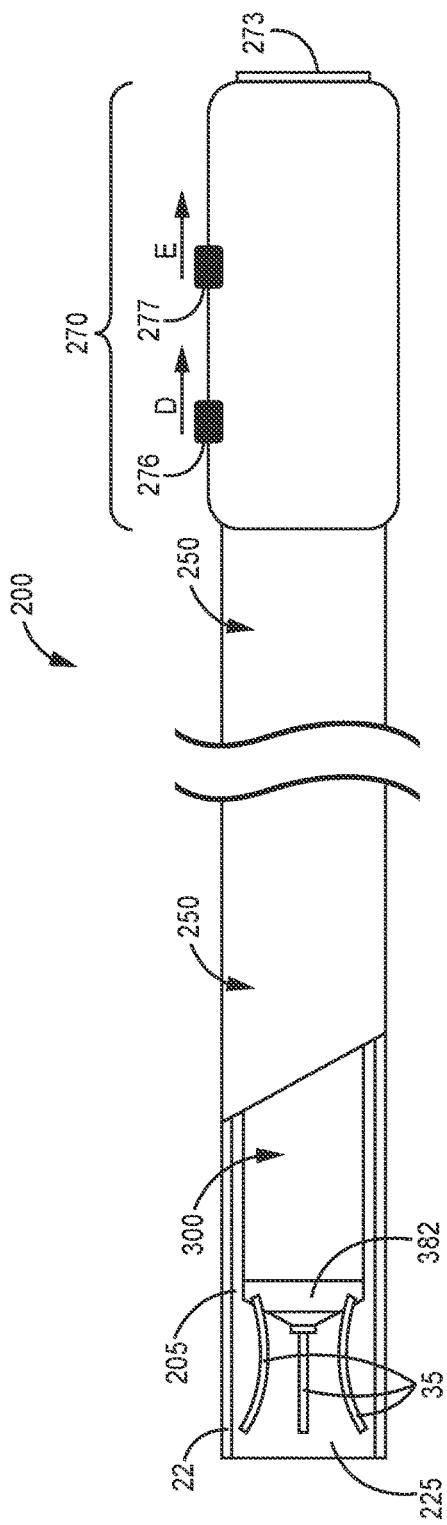
FIG. 4A is a plan view, with a partial cross-section view, of a catheter with an exemplary implantable medical device loaded into a lumen defined by an outer tubular member of the catheter, according to some embodiments of a system.

FIG. 4A is a plan view, with a partial cross-section view, of catheter 200 with an exemplary implantable medical device 300 loaded into a lumen 205 defined by an outer tubular member 250 of catheter 200, according to some embodiments of a system. FIG. 4A shows opening 225 terminating catheter lumen 205 at a distal end 22 of catheter 200. Device 300 is wholly contained within a relatively compact package, for example, as shown in the plan view of FIG. 4B, the entirety of which is configured for implant in close proximity to a pacing site. Thus, when catheter 200 is joined to shuttling apparatus, for example, as illustrated in FIGS. 5A-B, and apparatus collar 410 is mounted around the length of guidewire 100, as described above, catheter 200 can be shuttled along the length of guidewire 100 to position device 300 in proximity to an implant site. Catheter 200 may be configured like embodiments of the tool described in the commonly assigned United States Patent Application US 2015/0094668, such that an elongate inner assembly thereof (not shown) extends within lumen 205 defined by outer tubular member 250, from a proximal end of the inner assembly, which is secured to a handle 270 of catheter 200, to a distal end of the inner assembly that abuts a proximal end 381 (FIG. 4B) of device 300. With further reference to FIG. 4A, a proximal end of tubular member 250 is coupled to a control member 276 that is mounted in handle 270. Thus, when the operator moves control member 276, per arrow D, outer tubular member 250 retracts relative to the inner assembly and device 300 to deploy device 300 out from opening 225, which also ejects shuttle apparatus plug 430 through opening 225 and out from engagement within catheter lumen 205. As described in the aforementioned '668 reference, an elongate tether, which extends within the inner assembly and out from a proximal port 273 of catheter 200, may be temporarily attached to device 300, at proximal end 381, so the operator can maintain control over device 300 with the option to re-load the deployed device 300 back into catheter 200.

Figure 4B:
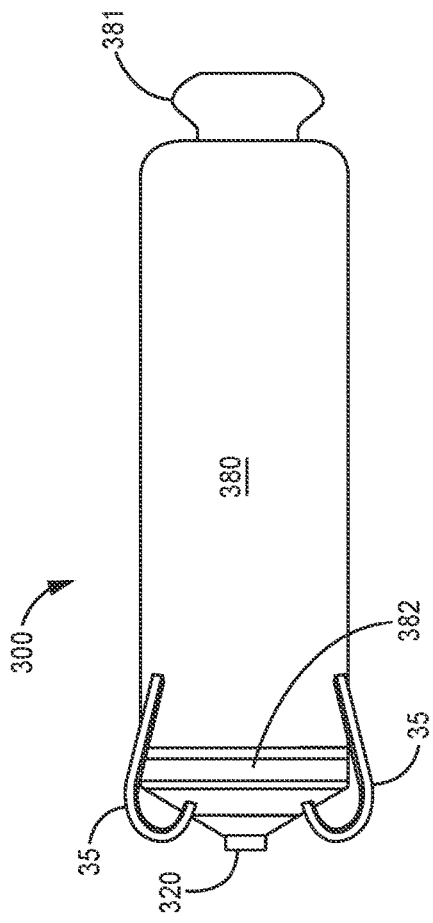
FIG. 4B is a plan view of the exemplary implantable medical device of FIG. 4A.

FIG. 4A further illustrates exemplary device 300 including a plurality of fixation tines 35, which are mounted to a distal end 382 of a hermetically sealed housing 380 of device 300, and are held in an extended condition within catheter lumen 205. FIG. 4B is a plan view of device 300 separate from catheter 200 where fixation tines 35 are shown in a relaxed condition. An electronic controller (not shown) of device 300, for example, a pulse generator and an associated power supply, are contained within housing 380, and an electrode 320 of device 300, also mounted to housing distal end 382, is electrically coupled to the controller via a hermetically sealed feedthrough assembly (not shown) such as is known in the art. Device housing 380, for example, formed from a biocompatible and biostable metal such as titanium, may be overlaid with an insulative layer, for example, medical grade polyurethane, parylene, or silicone, and device 300 may include another electrode (not shown), for example, formed by removing a portion of the insulative layer to expose the metallic surface of housing 380. The other electrode may function in conjunction with electrode 320 for bipolar pacing and sensing. Device tines 35, formed from a super-elastic material such as Nitinol, are configured to secure electrode 320 in intimate tissue contact at an implant site. Device 300 may include four tines 35, or as many as eight. In an exemplary embodiment, fixation tines 35 are integrally formed with one another, having been cut from Nitinol tubing, according to methods known in the art. After cutting the Nitinol tubing, tines 35 may be shaped by bending and holding tines 35 in the illustrated curvature while heat treating, according to methods known to those skilled in the art. Fixation tines 35 may be mounted to distal end 382 of device housing 380, for example, in a manner similar to that described for a fixation component 102 in a commonly assigned United States Patent Application 2012/0172690, which description is hereby incorporated by reference. The super-elastic nature of Nitinol allows tines 35 to elastically deform between the relaxed condition of FIG. 4B, and the extended condition of FIG. 4A, in which a free end of each tine 35 extends distally away from distal end 382 of device housing 380.

With further reference to FIGS. 1-3, and 5A-B, a proximal portion 430P of shuttle apparatus plug member 430 preferably includes a plurality of longitudinally extending grooves 433 formed therein, which are spaced apart from one another around a perimeter of proximal portion 430P, according to the spacing of device tines 35 around the perimeter of housing distal end 382. Thus, when plug member 430 is fitted within opening 225 of catheter 200 each groove 433 can receive a corresponding extended tine 35 of the loaded device 300, which is preferably positioned in closed proximity to opening 225. FIGS. 5A-B are a plan view, with a partial cut-away section, and a corresponding longitudinal cross-section view, respectively, that show the fitted plug member 430 and received device tines 35. According to some embodiments, for example, as illustrated in FIG. 2B and FIG. 5B, a base 3B of each groove 433 may be contoured to approximate a contour of each extended tine 35. According to some methods, extended tines 35 of device 300 may be engaged in grooves 433 of plug member 430 before device 300 is fully loaded into catheter 200, so that shuttle apparatus 400 is used to push device 300 through opening 225 to complete the loading of device 300.

According to some embodiments, and with reference to the longitudinal cross-section views of FIG. 2B (taken through line B-B of FIG. 2A) and FIG. 5B, pivot joint 420 of shuttle apparatus 400 may be formed by a pin 432 and a spring 42S. FIG. 2B and FIG. 5B illustrate pin 432 extending through an aperture 412 of a flange 411 of collar member 410, which extends in the aforementioned slot 403 of plug member 430. Plug member 430 is shown being spring biased to the unengaging position by pivot joint spring 42S, wherein a first end S1 of spring 42S is coupled to collar member flange 411, and a second end S2 of spring 42S is coupled to plug member 430. FIG. 2B and FIG. 5B further illustrate the movement of pin 432 within aperture 412, as pivot joint spring 47S is stretched against the bias thereof, from the unengaging position (FIG. 2B) to the engaging position (FIG. 5B) of plug member 430. Although spring 42S is illustrated as a coiled member, according to some alternate embodiments, spring 42S may be formed by an elastic band, for example, as illustrated in the embodiment of FIG. 10B. FIG. 10B is a longitudinal cross-section of a shuttle assembly 1400 that includes a collar member 1410 and plug member 1430, very similar to collar and plug member 410, 430 of assembly 400, being joined together by a pivot joint 1420, except that, instead of the coiled member illustrated for spring 42S of assembly 400, joint 1420 employs an elastic band as a spring 42B. The dashed line in FIG. 10B represents spring 42B stretched when plug member 1430 is moved to the engaging position.

Figure 6:
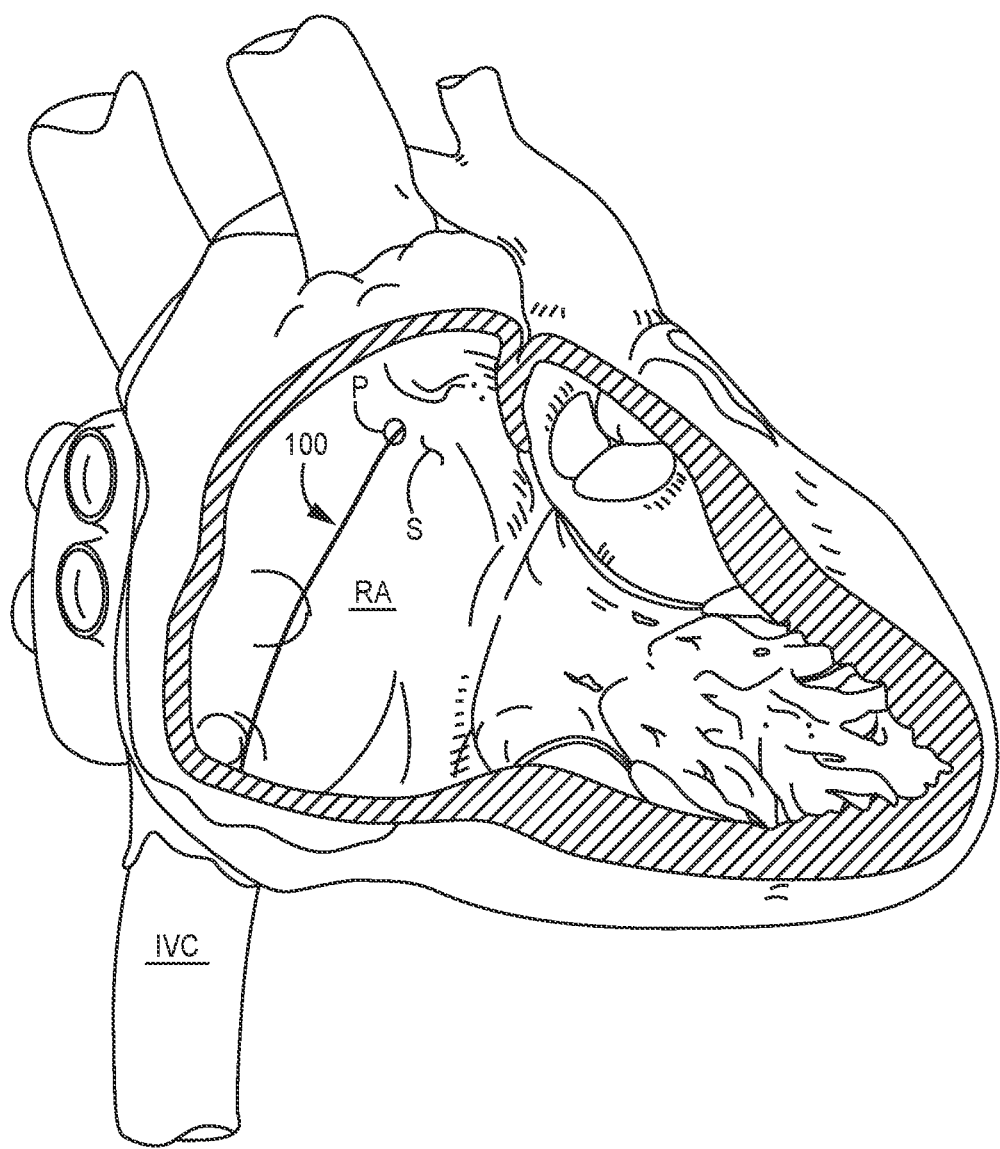
FIG. 6 is a schematic showing a guidewire extending into the right atrium of a patient's heart from the inferior vena cava.

FIG. 6 is a schematic showing guidewire 100 extending into the right atrium RA of a patient's heart from the inferior vena cava IVC, for example, having been inserted into the patient's venous system at a percutaneous access site formed in the patient's femoral vein, according to methods known in the art. FIG. 6 further illustrates a passageway P, which has been formed through an interatrial septum S, for example, in proximity to the Fossa Ovalis, and through which guidewire 100 extends to the left atrium of the patient's heart. With guidewire 100 positioned as shown, the operator, with the aid of shuttle apparatus 400, as illustrated in FIG. 5A, may guide catheter 200, with device 300 loaded therein, along guidewire 100 to a target implant site on a left side of the patient's heart. With reference to FIG. 5A, nose-cone 470 of shuttle apparatus 400, in concert with the profile of plug member 430, provides a tapered transition from guidewire 100 to catheter distal end 22 which facilitates passage of catheter 200 through passageway P, for example, as described below in conjunction with FIG. 9A.

To form passageway P, the operator may employ a dilator apparatus 500 (FIGS. 7A-B) delivered over guidewire 100. Such a dilator apparatus is also described in the commonly assigned U.S. patent application Ser. No. 15/387,224. After forming passageway P, dilator apparatus 500 may be retracted from over guidewire 100, which remains positioned as shown in FIG. 6, to make way for shuttle apparatus 400 with catheter 200 joined thereto.

FIG. 7A is a plan view of dilator apparatus 500, according to some embodiments; and FIG. 7B is a longitudinal cross-section view through a portion of dilator apparatus 500, according to some embodiments. FIGS. 7A-B illustrate dilator apparatus 500 including a relatively flexible elongate shaft 510 and a relatively rigid dilator tip 540 mounted thereto wherein a first portion 541 of dilator tip 540 extends around a distal end 512 of shaft 510, and a second portion 542 of dilator tip 540 extends from first portion 541 to a distal end 540D of dilator tip 540. Dilator tip first portion 541 is shown having an increasing taper from a first outer diameter OD1 (e.g., about 0.12 inch), at a proximal end 540P of dilator tip 540, to a larger second outer diameter OD2 (e.g., about 0.3 inch), in proximity to second portion 542 dilator tip 540; and dilator tip second portion 542 is shown having a decreasing taper from second outer diameter OD2 to a smaller third outer diameter OD3 (e.g., about 0.07 inch), in proximity to distal end 540D of dilator tip 540. FIG. 7B illustrates shaft 510 and dilator tip 540 including lumens 501, 504, respectively, which are in fluid communication with one another, for example, to provide a conduit for guidewire 100.

Figure 8A:
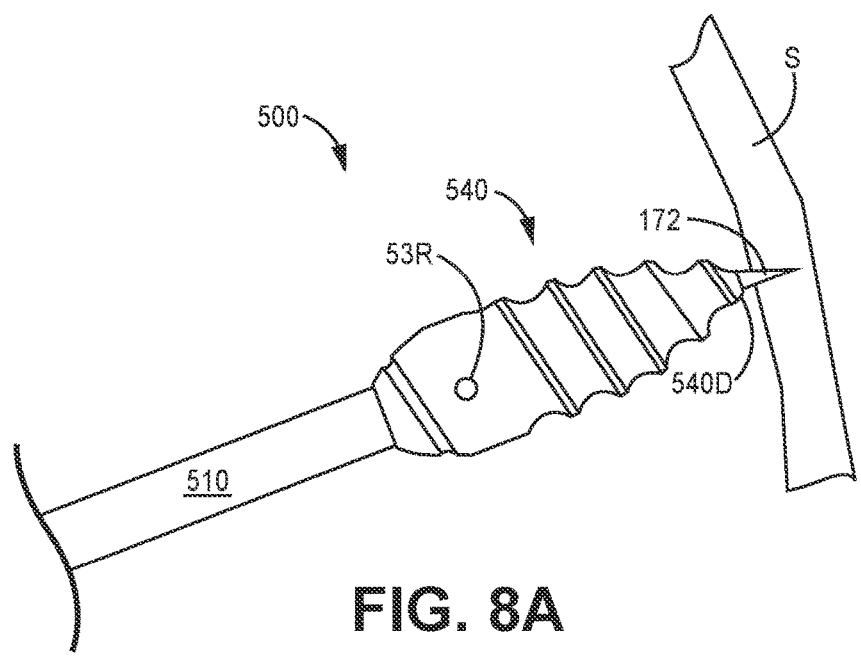
FIG. 8A is a conceptual diagram illustrating a dilator apparatus in conjunction with a septum.
Figure 8B:
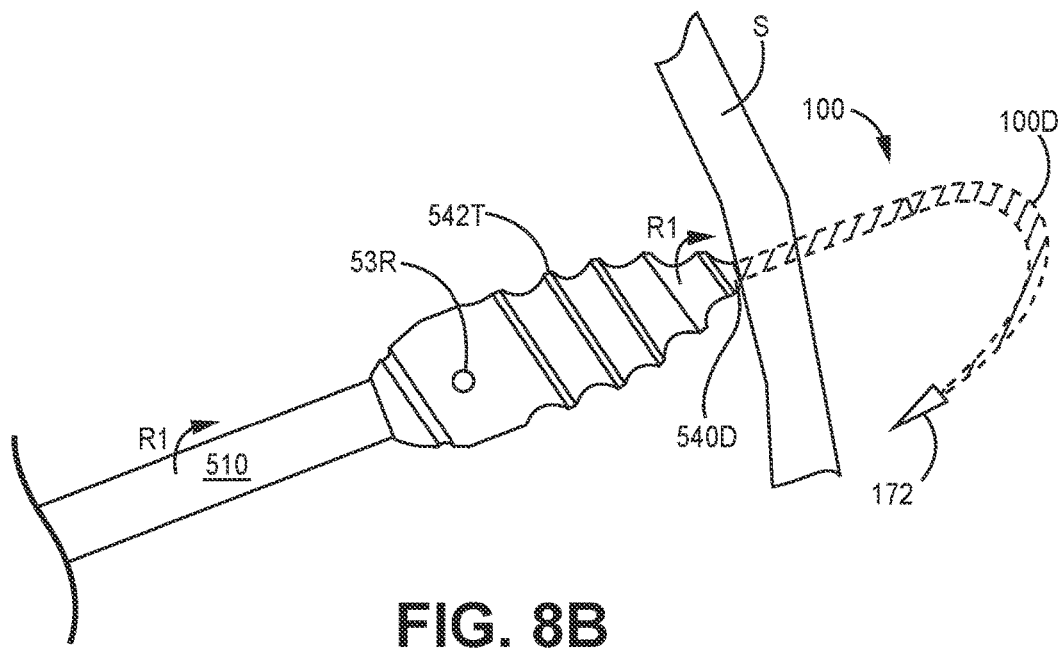
FIG. 8B is a conceptual diagram illustrating the dilator apparatus of FIG. 8A with a guidewire having been passed out though a distal opening to pierce through tissue of the septum.

Guidewire 100 in this context includes the above-described piercing distal-most point 103, so that the operator, after positioning dilator tip distal end 540D in close proximity to interatrial septum S, can advance guidewire 100 out through a distal opening 504O of dilator tip lumen 504 to pierce through the tissue of septum S, thereby forming an opening as a precursor to passageway P, for example, as shown in the schematics of FIGS. 8A-B. (A guidewire with a blunt, atraumatic distal tip may first be inserted within dilator apparatus lumens 501, 504 and employed to steer dilator apparatus 500 into the patient's right atrium, according to methods known in the art. Due to the atraumatic nature of dilator tip 540 with non-cutting thread 542T, the operator may advance dilator apparatus 500 directly within the patient's venous system without the need for an outer sheath.) According to some preferred embodiments dilator tip lumen 504 has a nominal diameter that is smaller than that of shaft lumen 501, for example, for a 'snugger' fit around wire 100, just proximal to wire distal tip 172, that can provide enhanced back-up support for tip 172, when the operator advances tip 172 out through distal opening 504O to pierce through septum S. Thus, in FIG. 7B, dilator tip lumen 504 is shown extending distally from a funnel-shaped entry 504E that increases an ease of passing wire distal tip 172 from shaft lumen 501 to dilator tip lumen 504. Guidewire 100, after having been passed out though distal opening 504O, to pierce through the tissue, can form a rail to guide dilator tip 540 as the operator rotates dilator 540, per arrow R1 of FIG. 8B, to create passageway P through septum S. FIG. 8B illustrates the above-described significantly flexible distal segment 100D of wire 570 flopped over, according to the pre-formed J-shape thereof, after tip 172 pierces through septum S, to prevent tip 172 from piercing into any other tissue on the left side of the patient's heart.

FIG. 7A further illustrates dilator tip second portion 542 including an external non-cutting thread 542T (e.g., having a radiused crest) formed along the decreasing taper. A pitch p of non-cutting thread 542T (FIG. 3B) may be about 0.125 inch in some embodiments. According to the illustrated embodiment, the operator, by engaging dilator tip distal end 540D with the tissue of septum S (FIG. 8B), at the opening previously formed by wire tip 172, and then by rotating dilator tip 540, per arrow R1, around a longitudinal axis thereof, causes dilator 540 to advance through the opening as a graduating diameter of non-cutting thread 542T (graduating from smaller third outer diameter OD3 to larger second outer diameter OD2) gradually increases the size of the opening to create, without undue trauma, passageway P. With further reference to FIGS. 7A-B, the increasing taper of dilator tip first portion 541 facilitates retraction of dilator 540 back through the passageway, for example, since the tissue may have a relative toughness and elasticity to cause some contraction of the formed passageway P. In some embodiments, as shown in FIG. 7A, dilator tip first portion 541 also includes an external non-cutting thread 541T formed along the increasing taper, to further facilitate retraction of dilator tip 540 back through passageway P, via rotation thereof around the longitudinal axis, for example, per arrow R2 in the schematic of FIG. 8C.

In FIG. 7A, a proximal end of guidewire 100 is shown extending out from a proximal hub 550 of dilator apparatus 500, and having a tool 560 attached thereto for example, to facilitate the operator's handling of guidewire 100. Proximal hub 550, which is shown joined to a strain-relieved proximal end 511 of shaft 510, may be formed by a Tuohy-Borst type fitting with a side-port known to those skilled in the art. FIG. 7A further illustrates an insertion stop 557, for example, being formed by a polymer tube, fitted around the proximal end of guidewire 100, between hub 550 and tool 560, so that tool 560 will abut stop 557 to prevent guidewire 100 from sliding distally in lumens 501, 504 before the operator is ready to advance piercing distal-most point 103 through septum S. After the operator has positioned distal end 540D of dilator 540 adjacent septum S, the operator can remove insertion stop 557 from guidewire 100; and, as illustrated in FIG. 7A, insertion stop 557 may be tethered to proximal end 511 of shaft 510, for example, to hub 550, so the operator cannot misplace it.

Figure 8C:
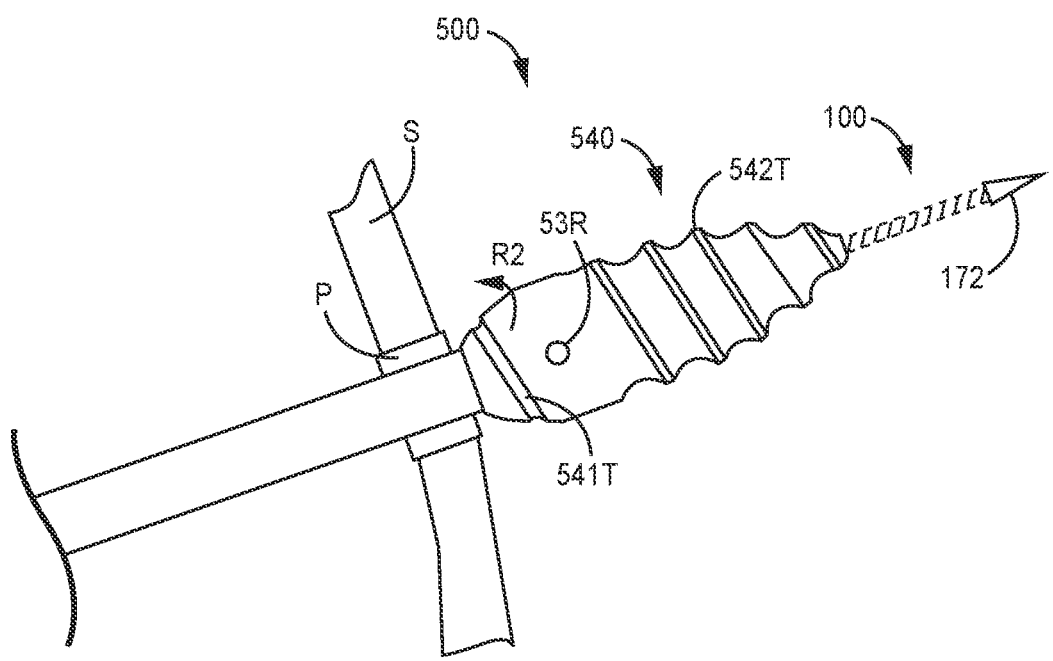
FIG. 8C is a conceptual diagram illustrating the dilator apparatus of FIG. 8A advanced through the septum along the guidewire to form a passageway.

According to an exemplary embodiment of dilator apparatus 500, shaft 510, which may have a nominal outer diameter of about 0.12 inch and extend over a length of up to approximately 100 cm, from proximal end 511 to distal end 512, is formed by a stainless steel braid-reinforced medical grade polymer, for example, one or more appropriate grades of polyether block amide, which are arranged for decreasing stiffness from proximal end 511 to distal end 512 (e.g., including PEBAX® 3533, 4033, 6333, and 7233), and has a fluoropolymer (e.g., PTFE) or a polyether block amide material lining lumen 501. A length of dilator tip 540, from proximal end 540P to distal end 540D may be up to about 1 inch (2.5 cm). Dilator tip 540, for example, formed from a relatively rigid medical grade plastic that has a relatively low surface friction (e.g., polyoxymethylene or polyamide), may be over-molded onto shaft distal end 512, or machined or molded as a separate component, which is then secured to shaft distal end 512. FIGS. 8A-C further illustrate dilator tip 540, according to some embodiments, including a radiopaque marker 53R embedded therein, for example, a tubular band of 90/10 Platinum/Iridium, which allows the operator to visualize, via fluoroscopy, the rotation of dilator tip 540.

Figure 9A:
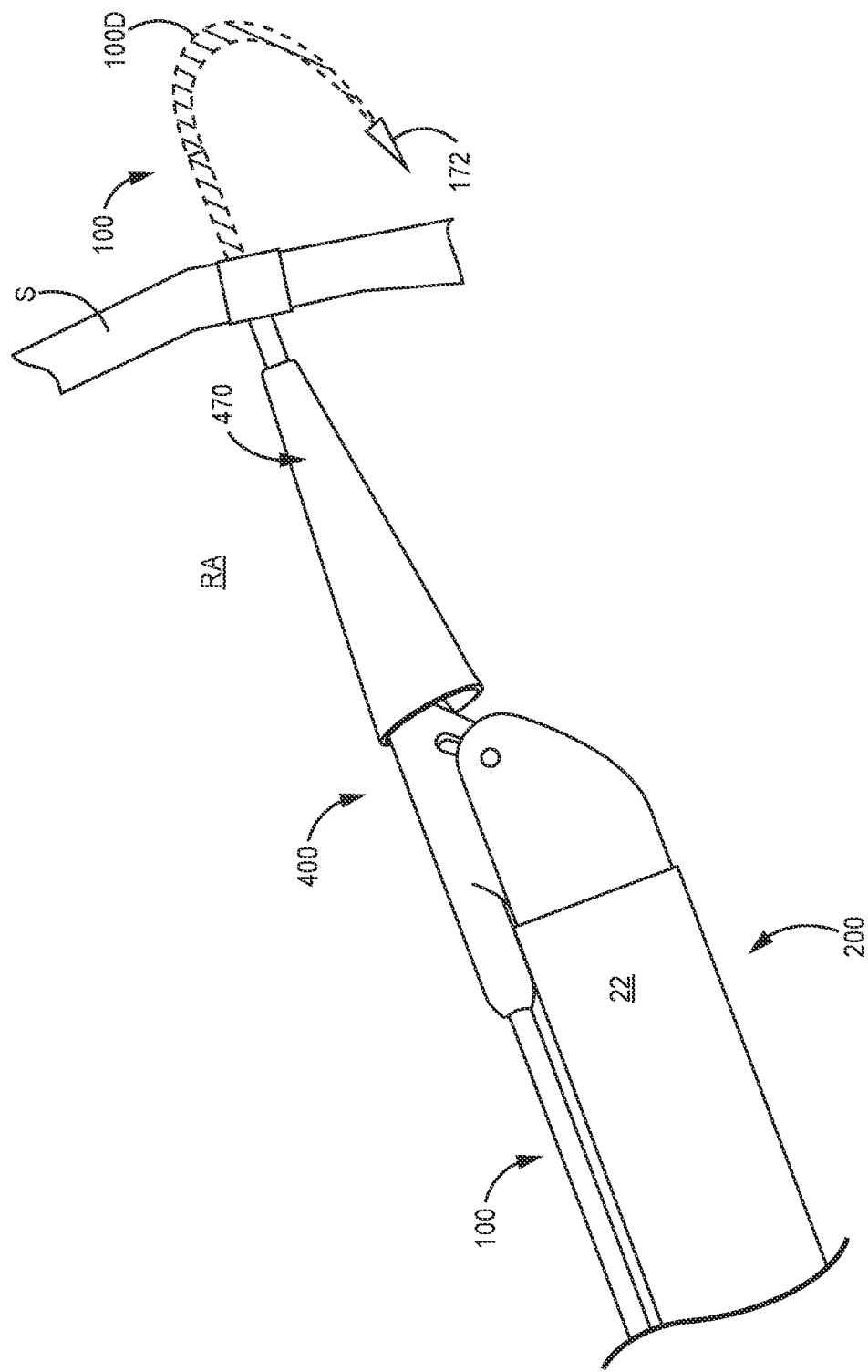
FIGS. 9A and 9B are schematics illustrating movement of a shuttling catheter along a guidewire and through a passageway, via a shuttle apparatus, after a dilator apparatus has been retracted from over the guidewire and removed from the patient's body, according to some methods.
Figure 9B:
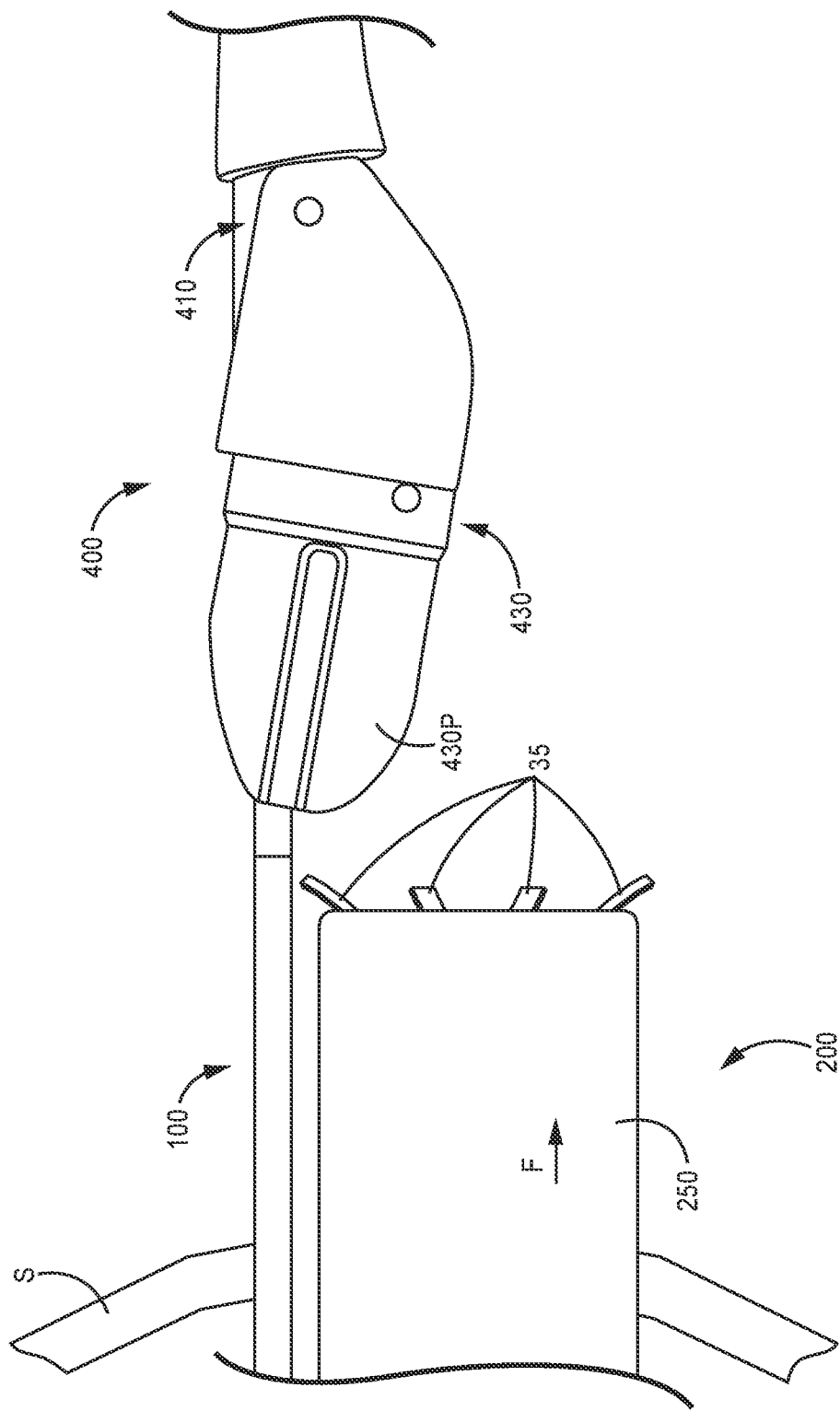
Figure 10A:
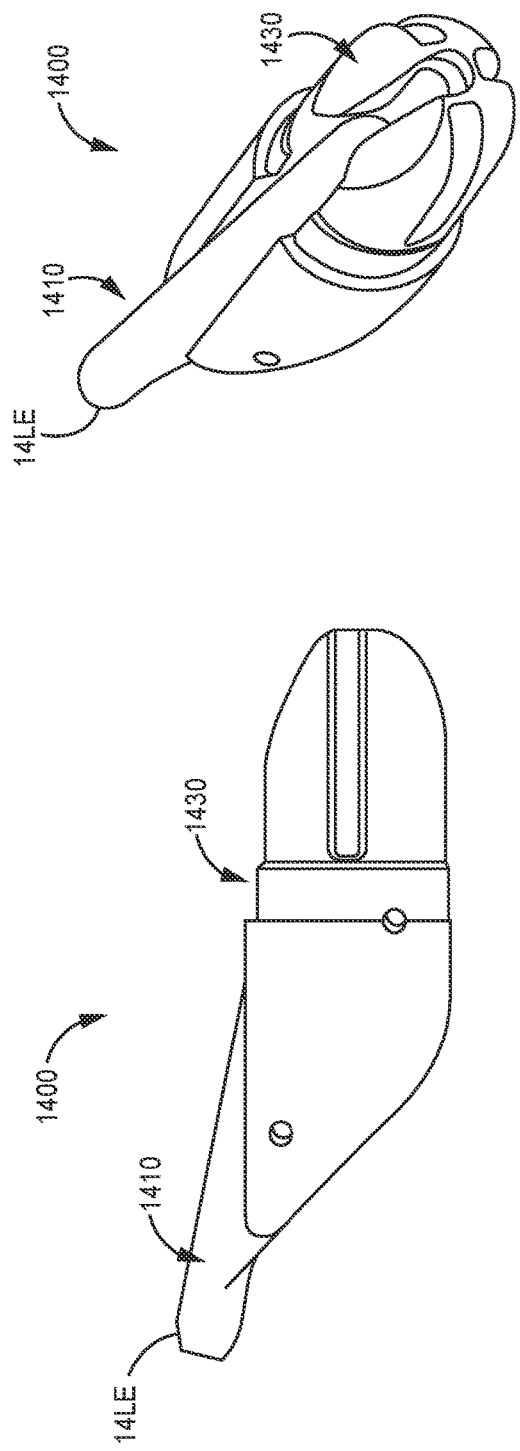
Figure 10B:
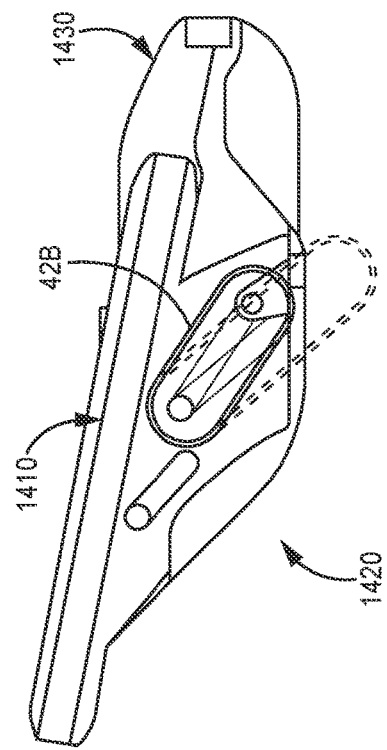

FIGS. 9A-B are schematics to describe the shuttling catheter 200 along guidewire 100 and through passageway P, via shuttle apparatus 400, after dilator apparatus 500 has been retracted from over guidewire 100 and removed from the patient's body, according to some methods. It should be noted that of FIGS. 9A-B and the ensuing description provide one exemplary context and a corresponding set of method steps for using shuttle apparatus 400 that should not limit embodiments and methods of the present invention.

FIG. 9A illustrates catheter 200 (with device 300 loaded therein) joined to shuttle apparatus 400, for example, as described above in conjunction with FIGS. 5A-B, wherein shuttle apparatus 400 is mounted in sliding engagement around guidewire 100, and has been moved along guidewire 100 to shuttle catheter 200 into the right atrium RA of the patient's heart. FIG. 9A further illustrates shuttle assembly nose cone 470 in proximity to passageway P. After passageway P is formed, the tissue of septum S may contract somewhat due to the aforementioned relative toughness and elasticity of the tissue, thus nose cone 470 is useful in providing a tapered transition so that shuttle apparatus 400 can again dilate passageway P to allow passage of catheter distal end 22 therethrough. Alternately, or in addition, with reference back to FIGS. 1A-B, extension distal segment 450D provides a tapering flexibility and tracking over guidewire 100 that can also facilitate movement of shuttle assembly through passageway P. According to alternate embodiments, for example, as shown in FIGS. 10A-C, nose cone 470 is not included. FIGS. 10A-C illustrate shuttle assembly 1400 that includes collar member 1410, very similar to collar member 410 of assembly 400, except that a leading edge 14LE of collar member 1410 (FIG. 10A) has an enhanced taper so that nose cone 470 is not necessary. However, with reference to FIG. 10C, shuttle assembly 1400 preferably includes extension 450, like assembly 400. FIG. 10C further illustrates assembly 1400 including radiopaque marker 472 joined to extension distal segment 450D in proximity to collar member 1410.

With reference to FIG. 9B, once the operator has passed catheter distal end 22 through passageway P, the operator may retract outer tubular member 250, via control member 276 (FIG. 4A), to partially deploy device 300, which ejects shuttle apparatus plug member 430 out from catheter opening 225, thereby detaching/separating catheter 200 and device 300 from guidewire 100. FIG. 9B shows plug member 430 of shuttle assembly 400 moved back into the unengaging position, described above in conjunction with FIGS. 1 and 2. Once catheter 200 is separated from shuttle apparatus 400, the operator may advance, per arrow F, outer tubular member 250 of catheter 200 relative to device 300, which may be held in place via the aforementioned tether, to re-load an entirety of device 300 in catheter 200, for example, as depicted in FIG. 2A. With device 300 re-loaded, the operator may then steer catheter 200, independent of guidewire 100 into proximity with a target implant site on the left side of the patient's heart. With reference back to FIG. 4A, catheter 200 may include a steering assembly, for example, including a pull wire, which the operator can manipulate by moved a control member 277 of catheter handle 270, per arrow E. The general construction of a suitable steering assembly for catheter 200 is known in the art and described in the aforementioned '668 reference. After the operator deploys device 300 at the implant site, catheter 200 may be withdrawn from the patient's body, followed by guidewire 100. As described above, in some embodiments, shuttle apparatus 400 is stopped from sliding off of guidewire 100 by the enlarged dimension of distal tip 172, so that apparatus 400 can be withdrawn from the patient's body along with guidewire 100. Alternately, in embodiments that include the relatively long extension proximal segment 450P (FIG. 1B), for example, up to about 120 cm, as described above, the operator may grasp extension proximal segment 450P to remove apparatus 400 independent of guidewire 100. With further reference to FIG. 9B, the orientation of plug member 430, with respect to collar member 410 of shuttle apparatus 400, in the unengaging position, and a contour of plug member proximal portion 430P can prevent shuttle apparatus 400 from hanging up on any features of the venous system during withdrawal therefrom.

The shuttle assembly 400 allows a leadless pacing device (e.g. Micra™) delivery system to be driven over a wire. It also eliminates the need to have a long, large French size introducer. The shuttle assembly 400 uniquely facilitates over-the-wire (OTW) guidance. It also allows for easy removal.

The present disclosure can be inserted in a conventional catheter delivery system. Specifically, the shuttle assembly 400 is inserted into the Micra™ cup straddling the tines of the Micra.

A 0.035" guide wire with a ball (or step) on the distal end is inserted into the vasculature (typically the femoral vein). It is advanced into a heart chamber.

The proximal end of the guide wire is inserted into the system.

The delivery system is then delivered over-the-wire.

After navigating to near the final position, the shuttle assembly 400 is no longer needed and is ejected. This is accomplished by temporarily, partially deploying the Micra thereby pushing the Periscope or (also referred to as shuttle assembly 400) out of the cup. After being ejected, the Periscope retracts and pivots to a more compact shape to facilitate later removal. The Micra is then retracted back into the cup.

Thus, the Periscope is "parked" out of the way.

The Micra is then directed to the desired position and deployed.

After successful Micra deployment, the delivery catheter is removed.

The 0.035" guide wire is then withdrawn. The ball on the distal end of the guide wire pulls the Periscope out of the body.

A. A 0.035" guide wire with a ball (or step) on the distal end.

B. The Periscope has a vertical extension/retraction feature as well as a pivoting feature.

Other embodiments have been produced that utilize 180 degree rotation.

C. The vertical extension feature allows the guide wire lumen to be along the outside of the Micra cup.

D. Once the cup is no longer present (e.g. the Periscope has been ejected from the cup) the vertical extension retracts via a spring or rubber band.

E. The vertical travel actually happens along a slight angle. This design feature is important because it prevents the Periscope from opening if the proximal end encounters resistance as it is removed from the body. Any resistance actually forces the Periscope to close more tightly.

F. The unique construction also allows for a pivot action.

G. The retracting/pivoting positions the wire lumen to be almost co-axial with the proximal end of the Periscope. This is important because it allows the Periscope to be retracted out of the body without getting hung up.

In the foregoing detailed description, the invention has been described with reference to specific exemplary embodiments. However, it may be appreciated that various modifications and changes can be made without departing from the scope of the invention as set forth in the appended claims.

We claim:

1. A method comprising:
rotating a plug member of an apparatus relative to a collar member of the apparatus via a pivot joint that couples the plug member to the collar member so that a longitudinal axis of the plug member extends approximately parallel to a longitudinal axis of the collar member;
inserting the rotated plug member of the apparatus into an opening of a catheter so that the catheter is detachably joined to the apparatus;
inserting a proximal end of a guidewire into the collar member of the apparatus so that the collar member is mounted in sliding engagement around the guidewire; and
pushing the catheter relative to the guidewire, after inserting the plug member into the opening of the catheter, and after inserting the proximal end of the guidewire into the collar member.

2. The method of claim 1, wherein the plug member further comprises a raised edge limiting a depth to which the plug member extends past the opening of the catheter when fitted therein.

3. The method of claim 1, further comprising an extension extending from an end of the collar member and along the longitudinal axis thereof.

4. The method of claim 1, further comprising a relatively soft nose cone extending distally from the collar member.

5. The method of claim 1, wherein a medical device is loaded in the catheter in proximity to the opening thereof.

6. The method of claim 5, wherein the medical device comprises one or more tines.

7. The method of claim 6, further comprising orienting the catheter around a longitudinal axis thereof to align the one or more tines of the loaded medical device with one or more corresponding longitudinally extending grooves of the plug member of the apparatus, each of the one or more grooves being sized to receive a corresponding tine of the one more tines therein when the rotated plug member is inserted into the opening of the oriented catheter.

8. The method of claim 6, further comprising engaging the one of more tines of the medical device with one or more corresponding longitudinally extending grooves formed in the plug member of the apparatus after rotating the plug member and before inserting the rotated plug member into the opening of the catheter, wherein, by inserting the rotated plug member into the opening of the catheter, the device is loaded into the catheter.

9. The method of claim 5, further comprising:
shuttling the catheter with the medical device loaded therein along a length of the guidewire and into proximity with an implant site in a patient, the plug member of the apparatus being inserted into the opening of the catheter, and the collar member of the apparatus being mounted in sliding engagement around the guidewire;
ejecting the plug member from the opening of the catheter after shuttling the catheter into proximity with the implant site thereby separating the catheter from the guidewire; and
removing the guidewire and the ejected apparatus out from a body of the patient independent of the catheter.

10. The method of claim 9, further comprising steering the catheter, independent of the guidewire, to the implant site to deploy the medical device at the implant site, after separating the catheter from the guidewire.

11. The method of claim 9, further comprising:
forming a passageway through an interatrial septum with a dilator assembly and the guidewire before shuttling the catheter;
removing the dilator assembly from over the guidewire and out from the body of the patient, after forming the passageway and before shuttling the catheter, leaving the guidewire in the body so that the length thereof, over which the catheter is shuttled, extends through the passageway.

12. The method of claim 9, wherein ejecting the plug member comprises moving the plug member to a disengaging position at which the longitudinal axis of the plug member extends at an angle with respect to the longitudinal axis of the collar member.

13. The method of claim 12, wherein the pivot joint is spring biased to the disengaging position of the plug member.

14. The method of claim 13, wherein the plug member includes a longitudinally extending slot formed therein, the slot being sized to receive the length of the guidewire therein, when the plug member is in the disengaging position.

15. The method of claim 14, wherein the collar member includes a flange to which the pivot joint is mounted, the flange extending within the slot of the plug member.

16. The method of claim 14, wherein the pivot joint includes a spring, a first end of the spring being coupled to the flange and a second end of the spring being coupled to the plug member.

* * * * *